United States Patent [19]

Werner

[11] 4,255,429

[45] Mar. 10, 1981

[54] N-QUINAZOLINYLPIPERIDINYL-LACTAMS

[75] Inventor: Lincoln H. Werner, Summit, N.J.

[73] Assignee: Ciba-Geigy Corporation, Ardsley, N.Y.

[21] Appl. No.: 115,634

[22] Filed: Jan. 28, 1980

Related U.S. Application Data

[63] Continuation-in-part of Ser. No. 46,062, Jun. 6, 1979, abandoned, and a continuation-in-part of Ser. No. 944,057, Sep. 20, 1978, abandoned.

[51] Int. Cl.³ .................. A61K 31/505; C07D 401/14
[52] U.S. Cl. ................. 424/251; 260/243.3; 260/244.4; 544/230; 544/291
[58] Field of Search ............. 260/243.3; 424/251; 544/230, 291

[56] References Cited

U.S. PATENT DOCUMENTS 3,635,979  1/1972  Hess ................................ 544/291

FOREIGN PATENT DOCUMENTS 2321890  4/1977  France.

Primary Examiner—Paul M. Coughlan, Jr.
Attorney, Agent, or Firm—Theodore O. Groeger

[57] ABSTRACT

N-[1-(4-amino-2-quinazolinyl)-3- or 4-piperidinyl]-lactams, e.g., those of the formula

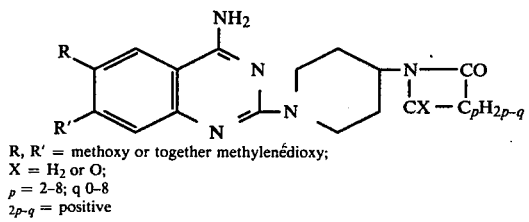

R, R' = methoxy or together methylenedioxy;
X = H$_2$ or O;
$p$ = 2-8; q 0-8
$2p$-$q$ = positive and salts thereof are antihypertensive agents.

10 Claims, No Drawings

N-QUINAZOLINYLPIPERIDINYL-LACTAMS

CROSS-REFERENCE TO RELATED APPLICATION

This is a continuation-in-part of application Ser. No. 46,062, filed June 6, 1979 (now abandoned) and, a continuation-in-part of application Ser. No. 944,057, filed Sept. 20, 1978 (now abandoned).

BACKGROUND OF THE INVENTION 1-(4-amino-2-quinazolinyl)-piperidines and derivatives thereof containing in the piperidine-4-position "alkyl...alkoxy...hydroxy, hydroxyalkyl...phenyl, benzyl (and) 4-phenyl-4-carboxylic acid alkyl ester" are "hypotensive agents" according to Pat. No. 3,511,836 and 3,635,474. Surprisingly, the compounds according to this invention, containing the lactam-nitrogen atom in the piperidine-3 or 4-position, exhibit superior hypotensive and antihypertensive activity by way of the α-blocking mechanism, and a lesser tendency towards the development of tolerance.

SUMMARY OF THE INVENTION

The present invention concerns and has for its object the provision of new N-[1-(4-amino-2-quinazolinyl)-3 or 4-piperidinyl]-lactams, more particularly of those corresponding to Formula I.

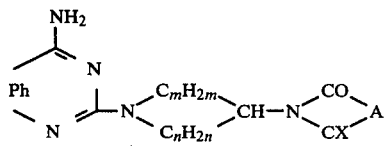

wherein Ph is 1,2-phenylene, unsubstituted or substituted by up to 3 lower alkyl or lower alkoxy groups, or by one lower alkylenedioxy group, each of m and n is an integer from 1 to 3, but $m+n=4$, X represents 2 hydrogen atoms or oxo and A is lower alkylene, 4 to 7 ring-membered cycloalkylene, cycloalkyl-lower alkylene, spirocycloalkane-lower alkylene, HPh-lower alkylene or Ph; of pharmaceutically acceptable acid addition salts thereof, as well as of corresponding pharmaceutical compositions and of methods for the preparation and application of said products, which are useful antihypertensive α-blocking agents (reducing the resistance of peripheral blood flow) suitable, for example, in the treatment or management of hypertension and/or congestive heart failure.

DESCRIPTION OF THE PREFERRED EMBODIMENTS

A substituted 1,2-phenylene group Ph, present in the quinazoline and/or lactam moiety, is preferably mono-, di- or trisubstituted by lower alkyl, e.g., methyl, ethyl, n- or i-propyl or -butyl; or lower alkoxy, e.g., methoxy, ethoxy, n- or i-propoxy or -butoxy; or monosubstituted by lower aklylenedioxy, e.g., methylenedioxy, 1,1- or 1,2-ethylenedioxy. Said substituents occupy preferably the 6,7- or 6,7,8-quinazolinyl positions therein.

The alkylene groups $C_mH_{2m}$ and $C_nH_{2n}$, separating the adjacent nitrogen atom from the methine group by 1 to 3 carbon atoms, represent above all ethylene each, but also methylene and 1,3-propylene.

A lower alkylene radical "A" is preferably ethylene, 1,3-propylene, 2,2-di-(methyl, ethyl, n-propyl or n-butyl)-1-ethylene or -1,3-propylene, 2,3- or 1,4-butylene.

A cycloalkylene, cycloalkyl-lower alkylene or spirocycloalkane-lower alkylene radical is 4 to 7 ring-membered each and represents, for example, 1,2-cyclobutylene, 1,2- or 1,3-(cyclopentylene, cyclohexylene or cycloheptylene); 1- or 2-(cyclopentyl or cyclohexyl)-(ethylene or 1,3-propylene); 1- or 2-spirocyclo-(butane, pentane or hexane)-(ethylene or 1,3-propylene).

The phenyl-lower alkylene or 1,2-phenylene, i.e. the H Ph-lower alkylene or Ph-radical "A" is preferably ring-unsubstituted, or but monosubstituted by said alkyl, alkoxy or alkylenedioxy groups, and represents, for example, 1-phenylethylene, 2-phenyl-1,3-propylene, 1- or 2-(tolyl or anisyl)-(ethylene or 1,3-propylene); 1,2-phenylene, 3- or 4-(methyl or methoxy)-1,2-phenylene or 4,5-methylenedioxy-1,2-phenylene.

As used above and hereinafter in connection with organic radicals or compounds respectively, the term "lower" defines such with up to 8, preferably up to 4, and advantageously 1 or 2 carbon atoms.

The basic compounds of Formula I form acid addition salts, preferably with the pharmaceutically acceptable acids listed below.

Said compounds of the invention exhibit valuable pharmacological properties, for example, hypotensive, antihypertensive and vasodilating activity. This is demonstrable in animal tests, using advantageously mammals, e.g. rats, cats or dogs, as test objects. The animals may either be normotensive or hypertensive, e.g. genetically or renal hypertensive rats or dogs. Said compounds can be applied to them enterally or parenterally, advantageously orally, subcutaneously, intravenously, intraperitoneally or intraduodenally, for example within gelatin capsules or in the form of starchy suspensions or aqueous solutions respectively. The applied dosage may range between about 0.1 and 100 mg/kg/day, preferably between about 1 to 75 mg/kg/day, advantageously between 5 and 50 mg/kg/day. The lowering effect on the blood pressure is recorded either directly by means of a catheter, e.g. placed in the rat's caudal or dog's femoral artery, and a transducer, expressing the blood pressure prior and after dosing in mm/Hg, or indirectly by sphygmomanometry, e.g. at the rat's tail. Thus, for example, 1-[4-(4-amino-6,7-dimethoxy-2-quinazolyl)-4-piperidinyl]-pyrrolidin-2,5-dione, or its pharmaceutically acceptable salts, which are representative members of the compounds of the invention, exhibit in said tests significant antihypertensive effects of high magnitude. Accordingly, the compounds of the invention are useful antihypertensive agents with no or minimal effects on the heart rate and thus applicable in the treatment or management of essential or renal hypertension and/or congestive or chronic heart failure in mammals. They are also useful intermediates in the preparation of other valuable products, especially of pharmacologically active compositions.

Preferred are compounds of Formula I, wherein Ph is 1,2-phenylene, unsubstituted or substituted by up to 3 alkyl or alkoxy groups with up to 4 carbon atoms or one alkylenedioxy group with up to 2 carbon atoms; each of m and n is an integer from 1 to 3, but $m+n=4$; X represents 2 hydrogen atoms or oxo and A is lower alkylene, 4 to 7 ring-membered cycloalkylene, cycloalky-lower alkylene, spirocycloalkane-lower alkylene, HPh-lower alkylene or Ph; or a pharmaceutically acceptable acid addition salt thereof.

Particularly useful are compounds of Formula I, in which Ph is 1,2-phenylene, mono-, di- or tri-(alkyl or alkoxy)-1,2-phenylene or alkylenedioxy-1,2-phenylene; wherein alkyl or alkylene contains up to 2 carbon atoms; each of $C_mH_{2m}$ and $C_nH_{2n}$ is ethylene, X represents 2 hydrogen atoms or oxo and A is lower alkylene, or 5 or 6 ring-membered 1,2-cycloalkylene or (cycloalkyl, spirocycloalkane or phenyl)-alkylene with up to 8 carbon atoms each, or a pharmaceutically acceptable acid addition salt thereof.

Preferred compounds of the invention are those of Formula II

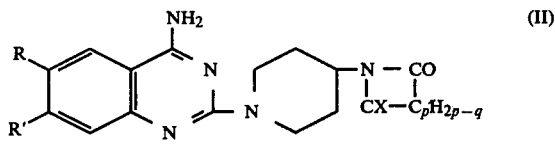

wherein R and R' are methoxy or (together) methylenedioxy, X represents two hydrogen atoms or oxo, $C_pH_{2p-q}$, is alkylene, phenylalkylene or spirocycloalkane-alkylene wherein p is an integer from 2 to 8, 0 is the integer 0, 2 or 8, and 2p-q is positive, or a pharmaceutically acceptable acid addition salt thereof.

Most preferred are compounds of Formula II, wherein each of R and R' are methoxy, X is oxo and $C_pH_{2p-q}$ is ethylene, phenylethylene or 1,3-propylene, or a pharmaceutically acceptable acid addition salt thereof.

The compounds of this invention are prepared according to conventional methods, for example, by condensing compounds of Formulae III and IV:

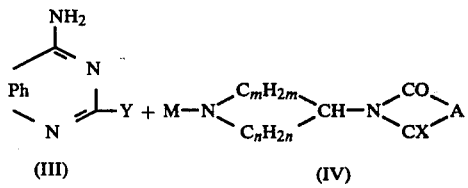

wherein Y is halogeno or lower alkythio and M is hydrogen or an alkali metal and, if desired converting any resulting compound of Formula I into another compound of the invention.

Said halogen atom Y, is advantageously chloro or bromo. A lower alkylthio group Y is preferably methylthio; and an alkali metal M is preferably sodium or potassium.

Said condensation occurs at temperatures above room temperature, for example, between about 100° and about 200° and/or in the presence of agents removing the acids generated, such as alkali metal carbonates or bicarbonates; or tert. amines, e.g. tri-lower alkylamines, pyridine or lower alkylated pyridines respectively.

Any resulting base can be converted into a corresponding acid addition salt, preferably with the use of a therapeutically acceptable acid or anion exchange preparation, or resulting salts can be converted into the corresponding free bases, for example, with the use of a base, such as a metal hydroxide, basic salt, ammonia, amine or cation exchange preparation, e.g. and alkali metal hydroxide or carbonate. Said acid addition salts are preferably such of pharmaceutically acceptable inorganic or organic acids, such as strong metalloidic acids, for example, hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, ethylenesulfonic, halogenbenzenesulfonic, toluenesulfonic, naphthalenesulfonic, sulfanilic or cyclohexylsulfamic acid. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The starting material of Formulae III and IV is known or, if new, its preparation is illustrated by the examples herein. Known starting materials are also described, together with their precursors, inter alia, in U.S. Pat. Nos. 3,511,836; 3,769,286 and Applicant's U.S. Pat. No. 4,000,287, as well as the references cited therein. In case mixtures of geometrical or optical isomers of compunds I are obtained, these can be separated into the single isomers by methods in themselves known, e.g. by fractional distillation, crystallization and/or chromatography. Racemic products can likewise be resolved into the optical antipodes, for example, by separation of diastereomeric sales thereof, e.g. by the fractional crystallization of d- or l-tartrates.

The above-mentioned reactions are carried out according to standard methods, in the presence or absence of diluents, preferably such are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage of the process is used as a starting material and any remaining steps are carried out, or the process is discontinued at any stage thereof, or in which the starting materials are formed under the reaction conditions, or in which the reaction components are used in the the form of their salts or optically pure antipodes. Mainly those starting materials should be used in said reactions that lead to the formation of those compounds indicated above as being especially valuable, e.g. those of Formula II.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with a) diluents, e.g. lactose, dextrose, sucrose, mannitol, sorbitol, cellulose and/or glycine, b) lubricants, e.g. silica, talcum, stearic acid, its magnesium or calcium salt and/or polyethyleneglycol, for tablets also c) binders, e.g. magnesium aluminum silicate, starch paste, gelatin, tragacanth, methylcellulose, sodium carboxymethylcellulose and/or polyvinylpyrrolidone, if desired, d) disintegrants, e.g. starches, agar, alginic acid or its sodium salt, enzymes of the binders or effervescent mixtures and/or e) absorbents, colorants, flavors and sweeteners. Injectable or inhalable compositions are preferably agueous isotonic solution or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition they may also contain other therapeutically valuable substances. Said compositions are prepared according to conventional mixing, granulating or coating methods respectively and contain about 0.1 to 75%, preferably 1 to 50%, of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 1 and 100 mm Hg.

Example 1

The mixture of 8.66 g of 4-amino-2-chloro-6,7-dimethoxyquinazoline, 6.6 g of 1-(4-piperidinyl)-pyrrolidine-2,5-dione, 9.4 g of diisopropylethylamine and 100 ml of dimethylformamide is stirred under nitrogen at 150° for 8 hours. The mixture is evaporated, the residue triturated with aqueous sodium carbonate and extracted with ethyl acetate. The extract is washed with water, dried, evaporated and the residue crystallized from ethanol. The crystals are dissolved in a mixture of ethanol and acetone, the solution neutralized with methane sulfonic acid and the precitate formed filtered off, dried and recrystallized from aqueous ethanol, to yield the 1-[1-(4-amino-6,7-dimethoxy-2-quinazolinyl)-4-piperidinyl]-pyrrolidin-2,5-dione monomesylate of the formula

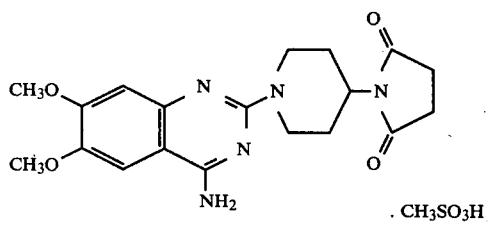

melting at 331° with decomposition.

The starting material is prepared as follows: The mixture of 20 g of succinic anhydride, 19 g of 4-aminopyridine, and 450 ml of xylene is refluxed for 24 hours with stirring. It is allowed to cool to room temperature and the solids are collected. They are extracted 3 times with 200 ml of methylene chloride at reflux and the combined extracts are evaporated and the residue recrystallized from ethanol, to yield the 1-(4-pyridyl)-pyrrolidin-2,5-dione.

11.36 g thereof are hydrogenated at 60° in the minimum amount of glacial acetic acid over 8 g of 10% palladium on carbon at 2.7 atm. The mixture is filtered, evaporated, the residue made basic with aqueous sodium carbonate, extracted with chloroform and the extract evaporated, to yield the 1-(4-piperidinyl)-pyrrolidin-2,5-dione melting at 133° to 134°.

Example 2

The mixture of 6.7 g of 4-amino-2-chloro-6,7-dimethoxyquinazoline, 5.5 g of 1-(4-piperidinyl)-piperidin-2,6-dione, 7.2 g of diisopropylethylamine and 75 ml of dimethylformamide is stirred under nitrogen for 8 hours at 150°. It is cooled to room temperature and filtered, the filtrate concentrated, the residue triturated with ethanol, filtered again and both precipitates combined. These solids are taken up in aqueous sodium carbonate, the mixture extracted with ethyl acetate, the extract washed with water, dried and evaporated. The residue is dissolved in warm ethanol, the solution acidified with methane sulfonic acid, the precipitate filtered off and recrystallized from aqueous ethanol, to yield the 1-[1-(4-amino-6,7-dimethoxy-2-quinazolinyl)-4-piperidinyl]-piperidin-2,6-dione monomesylate melting at 333°–334°.

The starting material is prepared as follows: The mixture of 34.2 g of glutaric anhydride, 28.2 g of 4-aminopyridine and 650 ml of xylene is refluxed with stirring for 6 hours. It is allowed to cool to room temperature, the solids are filtered off and extracted twice with 200 ml chloroform at reflux. The combined extracts are evaporated and the residue recrystallized twice from ethyl acetate to yield the 1-(4-pyridyl)-piperidine-2,6-dione melting at 153°–155°.

8.1 g thereof are hydrogenated in 100 ml of glacial acetic acid at 60° over 6.3 g of 10% palladium on charcoal at 2.9 atm, the mixture is filtered, evaporated and the residue treated with aqueous sodium carbonate. The mixture is extracted repeatedly with methylene chloride, and the combined extracts are evaporated to yield the 1-(4-piperidinyl)-piperidine-2,6-dione as a low melting, solvated material.

Example 3

The mixture of 4.79 g of 4-amino-2-chloro-6,7-dimethoxyquinazoline, 4.49 g of 4,4-dimethyl-1-(4-piperidinyl)-piperidin-2,6-dione, 4.24 g of anhydrous sodium carbonate and 75 ml of dimethylformamide is stirred at 150° under nitrogen for 6 hours. It is filtered, the filtrate evaporated, the residue dissolved in ethyl acetate and the solution washed with aqueous sodium carbonate and water. It is dried, evaporated, the residue triturated with isopropanol, filtered off and discarded. The filtrate is made strongly acidic with hydrogen chloride, the precipitate filtered off and triturated with 175 ml of boiling methanol, to yield the 1-[1-(4-amino-6,7-dimethoxy-2-quinazolinyl)-4-piperidinyl]-4,4-dimethyl-piperidin-2,6-dione monohydrochloride, melting at 279°–280° with decomposition.

The starting material is prepared as follows: The mixture of 19.3 g of 3,3-dimethylglutaric anhydride, 12.55 g of 4-aminopyridine and 350 ml of xylene is refluxed for 60 hours while stirring and simultaneous water separation. The hot xylene solution is decanted from some sirupy residue, cooled to room temperature, filtered and the residue recrystallized from ethanol, to yield the 4,4-dimethyl-2-(4-pyridyl)-piperidin-2,6-dione melting at 225°–226°.

20 g thereof are dissolved in 200 ml of glacial acetic acid at 60° and hydrogenated over 15 g of 10% palladium on carbon at 3.1 atm. The mixture is filtered, evaporated, the residue taken up in 6N aqueous sodium hydroxide with cooling and the mixture extracted with methylene chloride. The extract is evaporated and the residue recrystallized from a mixture of benezene and hexane, to yield the 4,4-dimethyl-1-(4-piperidinyl)-1-piperidin-2,6-dione melting at 162°–163°.

Example 4

The mixture of 70 g of 4-amino-2-chloro-6,7-dimethoxyquinazoline, 73.2 g of 8-(4-piperidinyl)-8-azaspiro[4,5]decan-7,9-dione, 62.1 g of anhydrous sodium carbonate and 800 ml of dimethylformamide is stirred under nitrogen at 135° for 8 hours. It is allowed to cool to room temperature, filtered and the filtrate evaporated. The residue is poured with stirring and cooling into 300 ml of water, the mixture diluted with 1400 ml of water and filtered. The solids are triturated with 1600 ml of ethyl acetate and 10 ml of saturated aqueous sodium carbonate. The organic layer is separated, dried, evaporated and the residue dissolved in 1,000 ml of ethyl acetate. The solution is acidified with hydrogen chloride, the precipitate filtered off and recrystallized from aqueous methanol, to yield the 8-[1-(4-amino-6,7-dimethoxy-2-quinazolinyl)-4-piperidinyl]-8-azaspiro[4,5]decan-7,9-dione hydrochloride melting at 277°–279° (dec.).

5 g thereof are suspended in 100 ml of water and 10 ml of 6N aqueous sodium hydroxide and the mixture is extracted with chloroform. The extract is washed with water, dried, evaporated, and the residue dissolved in 50 ml of ethanol with warming. 0.94 g of methane sulfonic acid are added, the precipitate is separated and recrystallized from aqueous ethanol, to yield the corresponding monomesylate melting at 307°–308°.

The starting material is prepared as follows: The mixture of 200 g of 3,3-tetramethyleneglutaric anhydride, 57 g of 4-aminopyridine and 1,500 ml of xylene is stirred and refluxed on a water separator for 3 days. After cooling slightly, the xylene solution is decanted from a small amount of oily material, and after cooling in an ice bath, the collected residue dissolved in 1,500 ml of boiling ethanol, the solution cooled to 5°, filtered and the residue dried, to yield the 8-(4-pyridyl)-8-azaspiro[4,5]decan-7,9-dione melting at 208°–211°.

The solution of 58 g thereof in 580 ml of glacial acetic acid is hydrogenated over 45 g of 10% palladium on carbon between 60° and 100° and 3.1 atm. After the theoretical amount of hydrogen has been absorbed, the mixture is filtered and evaporated. The residue is rendered alkaline with 6N aqueous sodium hydroxide and the mixture extracted with chloroform. The extract is washed with saturated aqueous sodium chloride, dried, evaporated and the residue dissolved in 325 ml of hot toluene. The solution is filtered, diluted with 400 ml of hexane, cooled and filtered, to yield the 8-(4-piperidinyl)-8-azaspiro[4,5]decan-7,9-dione melting at 141°–142°.

Example 5

The mixture of 5.39 g of 4-amino-2-chloro-6,7,8-trimethoxyquinazoline, 5.25 g of 8-(4-piperidinyl)-8-azaspiro-[4,5]decan-7,9-dione, 4.24 g of anhydrouus sodium carbonate and 75 ml of dimethylformamide is stirred at 150° for 8 hours. After cooling to room temperature it is filtered, the filtrate evaporated, the residue dissolved in ethyl acetate and the solution washed with aqueous sodium bicarbonate and water. It is dried, evaporated, the residue dissolved in 75 ml of ethyl acetate and allowed to crystallize. The crystals are dissolved in 50 ml of hot isopropanol and the solution acidified with hydrogen chloride to pH=1 and the precipitate filtered off, to yield the 8-[1-(4-amino-6,7,8-trimethoxy-2-quinazolinyl)-4-piperidinyl]-8-azaspiro[4,5]decan-7,9dione monohydrochloride melting at 225°–227°.

Example 6

The mixture of 2.39 g of 4-amino-2-chloro-6,7-dimethoxyquinazoline, 2.64 g of 3-(4-piperidinyl)-3-azaspiro-[5,5]-undecan-2,4-dione, 2.1 g anhydrous sodium carbonate and 25 ml of dimethylformamide is stirred under nitrogen at 150° for 10 hours. It is filtered, the filtrate evaporated, the residue dissolved in methylene chloride, the solution washed with aqueous sodium carbonate, dried, filtered and evaporated. The residue is triturated with 50 ml of isopropanol, the remainder taken up in isopropanol and the mixture acidified with hydrogen chloride, to yield the 3-[2-(4-amino-6,7-dimethoxy-2-quinazolinyl)-4-piperidinyl]-3-azaspiro[5,5]undecan-2,4-dione monohydrochloride melting at 290° (dec.).

The starting material is prepared as follows: The mixture of 25 g of 2,2-cyclohexane diacetic anhydride, 12.92 g of 4-aminopyridine, and 400 ml of xylene is refluxed for 25 hours using a water separator. The hot, supernatant xylene solution is decanted from an oil precipitate (which is discarded), cooled, filtered and the residue recrystallized from ethanol, to yield the 3-(4-pyridyl)-3-azaspiro[5,5]undecan-2,4-dione melting at 213°–215°.

13.8 g thereof are dissolved in 150 ml of glacial acetic acid and hydrogenated over 10 g of 10% palladium on carbon at 50°–60° and 1.7 atm. The mixture is filtered and the residue worked up as described in Example 4, to yield the 3-(4-piperidinyl)-3-azaspiro[5,5]undecan-2,4-dione, melting after recrystallization from benzene-hexane at 148°–149°.

Example 7

The mixture of 5.72 g of 4-amino-2-chloro-6,7-dimethoxyquinazoline, 5.65 g of 2-(4-piperidinyl)-2-azaspiro[4,4]nonan-1,2-dione, 6.16 g of diisopropylethylamine and 75 ml of dimethylformamide is stirred under nitrogen at 150° for 8 hours. It is evaporated, the residue partitioned between ethyl acetate and aqueous sodium carbonate, the organic solution washed with water, dried and evaporated. The residue is dissolved in ethanol and methane sulfonic acid added until the pH=1. The precipitate formed is filtered off and recrystallized from methanol and then from aqueous ethanol, to yield the 2-[1-(4-amino-6,7-dimethoxy-2-quinazolinyl)-4-piperidinyl]-2-azaspiro-[4,4]nonan-1,3-dione monomesylate melting at 278°–280°.

The starting material is prepared as follows: The mixture of 21.8 g of tetramethylenesuccinic anhydride (prepared from the diacid by refluxing with acetic anhydride), 12.1 g of 4-aminopyridine and 300 ml of xylene is refluxed on a water separator for 9 hours. The hot solution is filtered, cooled to 5° and the residue recrystallized from ethanol, to yield the 2-(4-pyridyl)-2-azaspiro[4,4]nonan-1,3-dione melting at 100°–103°.

16.76 g thereof are hydrogenated over 12 g of 10% palladium on carbon in 180 ml of glacial acetic acid at 60° and 3.2 atm. The mixture is filtered, evaporated, the residue made basic with aqueous sodium carbonate and extracted repeatedly with chloroform. The extracts are dried and concentrated to yield the 2-(4-piperidinyl)-2-azaspiro[4,4]nonan-1,3-dione melting at 119°–120°.

Example 8

The mixture of 4.8 g of 4-amino-2-chloro-6,7-dimethoxyquinazoline, 5.17 g of 1-(4-piperidinyl)-3-phenylpyrrolidin-2,5dione, 5.2 g of diisopropylethylamine and 75 ml of dimethylformamide is stirred under nitrogen at 150° for 8 hours. It is evaporated, the residue partitioned between ethyl acetate and aqueous sodium carbonate, the organic layer separated, dried and evaporated. The residue is dissolved in warm ethanol and acidified with methane sulfonic acid to pH=1. The precipitate formed on cooling is collected and recrystallized from aqueous ethanol to yield the 1-[1-(4-amino-6,7-dimethoxy-2-quinazolinyl)-4-piperidinyl]-3-phenylpyrrolidin-2,5-dione monomesylate melting at 239°–244° (dec.).

The starting material is prepared as follows: The mixture of 20.2 g of phenylsuccinic anhydride, 10.7 g of 4-aminopyridine and 300 ml of xylene is refluxed and stirred on a water separator for 6 hours. The hot solution is decanted from some gummy precipitate, and on cooling a precipitate separates. It is filtered off and recrystallized from ethanol, to yield the 3-phenyl-2-(4-pyridyl)-pyrrolidin-2,5-dione melting at 146°–147°.

20.6 g thereof are hydrogenated in 200 ml of glacial acetic acid over 14 g of 10% palladium on carbon at 60° and 3 atm. The mixture is filtered, evaporated and the residue dissolved in 75 ml of water. The solution is made basic with sodium carbonate and extracted repeatedly with ethyl acetate. The extract is washed with aqueous sodium carbonate, dried, evaporated and the residue recrystallized from a mixture of toluene and hexane, to yield the 1-(4-piperidinyl)-3-phenylpyrrolidin-2,5-dione melting at 119°–124°.

Example 9

The mixture of 5.39 g of 4-amino-2-chloro-6,7,8-trimethoxy-quinazoline, 4.32 g of 2-(4-piperidinyl)-isoindolin-1-one, 4.24 g of anhydrous sodium carbonate and 75 ml of dimethylformamide is stirred under nitrogen at 125°–130° for 16 hours. It is filtered, the filtrate evaporated, the residue dissolved in methylene chloride and the solution washed with aqueous sodium bicarbonate. The organic layer is separated, dried, and evaporated. The residue is suspended in refluxing isopropanol and acidified with hydrogen chloride to pH=1. The precipitate formed is filtered off and triturated with warm ethanol to yield the 2-[1-(4-amino-6,7,8-trimethoxy-2-quinazolinyl)-4-piperidinyl]-isoindolin-1-one monohydrochloride melting at 234° (dec.).

By heating in an analogous fashion 2.4 g of 4-amino-2chloro-6,7-dimethoxyquinazoline, 2.2 g of 2(-piperidinyl)-isoindolin-1-one, 2.0 g of anhydrous sodium carbonate and 20 ml of dimethylformamide, the 2-[1-(4-amino-6,7-dimethoxy-2-quinazolinyl)-4-piperidinyl]-isoindolin-1-one monohydrochloride is obtained, melting at 288°–289° (dec.).

The starting material is prepared as follows: The mixture of 150 g of 2-formylbenzoic acid, 85.2 g of 4-aminopyridine and 2,800 ml of toluene is refluxed on a waterseparator for 2.5 hours while stirring and stirring is continued at room temperature overnight. It is filtered and the residue washed with toluene to yield the 1-(4-pyridylamino)-3-oxo-phthalan melting at 215°–220°. [Analogously the 1-[3-pyridylamino)-3-oxophthalan is obtained from 3-aminopyridine; m.p. 150°–155°].

To the suspension of 278 g thereof in 4,700 ml of anhydrous ethanol, 96 g of sodium borohydride and added portionwise during 105 minutes while stirring at 18°. Stirring is continued at room temperature overnight, the mixture is filtered, the filtrate concentrated to a volume of 1,200 ml. cooled and the precipitate formed collected, to yield the 2-(4-pyridylaminomethyl)-benzoic acid melting above 250°.

180 g thereof are added to 1,400 ml of concentrated sulfuric acid during 40 minutes while stirring and allowing the temperature to rise to about 67°. The mixture is stirred for 1 hour at about 95°, cooled to 25°, and slowly poured onto 4 kg of ice. The mixture is neutralized with about 4,500 ml of aqueous ammonia, the precipitate formed filtered off and taken up in 2,300 ml of isopropanol and 600 ml of chloroform. The mixture is refluxed for 30 minutes, filtered hot, the filtrate cooled and the precipitate formed collected, to yield the 2-(4- pyridyl)-isoindolin-1-one.

The mixture of 30 g thereof, 400 ml of glacial acetic acid and 30 g of 10% palladium on charcoal is hydrogenated at about 65° and 3 atm until the theoretical amount of hydrogen has been absorbed. It is cooled to room temperature, filtered and evaporated. The residue is taken up in 6N aqueous sodium hydroxide, the mixture extracted with chloroform, the extract washed with saturated aqueous sodium chloride, dried and evaporated, to yield the 2-(4-piperidinyl)-isoin dolin-1-one melting at 144°–146°.

Example 10

The mixture of 4.4 g of 4-cyclohexyl-1-(4-piperidinyl)-piperidine-2,6- dione, 3.41 g of 4-amino-2-chloro-6,7-dimethoxyquinazoline and 100 ml of isoamyl alcohol is refluxed with stirring for 20 hours. After standing at room temperature for 18 hours it is filtered, the residue washed with isoamyl alcohol and diethyl ether, dried and dissolved in aqueous sodium carbonate. The solution is extracted with methylene chloride, the extract evaporated and 7.0 g of the residue dissolved in 75 ml of ethanol. After addition of 1.4 g methane sulfonic acid, another 125 ml of ethanol are added, the precipitate formed is filtered off and recrystallized from aqueous ethanol to yield the 1-[1-(4-amino-6,7-dimethoxy-2-quinazolinyl)-4-piperidinyl]-4-cyclohexyl-piperidin-2,6-dione monomesylate melting at 277°–279°.

The starting material is prepared as follows: The mixture of 22.4 g of 3-(p-chlorophenyl)-glutaric anhydride, 10.3 g of 4-aminopyridine, 350 ml of xylene and 1.5 g of methane sulfonic acid is refluxed on a water separator while stirring for 4 days. After the first day an additional 0.5 g of methane sulfonic acid is added and the hot solution is finally decanted from some gummy material. The crystals formed on cooling are filtered off, triturated with hot ethanol, cooled, filtered off again and dried to yield the 4-(p-chlorophenyl)-1-(4-pyridyl)-piperidin-2,6-dione melting at 204°–206°.

The mixture of 11 g thereof, 5.5 g of 10% palladium on carbon and 150 ml of glacial acetic acid is hydrogenated at 3 atm. and 120°–140° C. for 10 hours. After cooling the solution is filtered, evaporated, the residue dissolved in the minimum amount of water, the solution made basic with 2N aqueous sodium hydroxide and extracted with methylene chloride. The extract is washed with water and evaporated, to yield the 4-cyclohexyl-1-(4-piperidinyl)-piperidine-2,6-dione; the hydrochloride thereof melts at 284°–285° with decomposition.

Example 11

The mixture of 4.57 g of 4-amino-2-chloro-6,7-dimethoxyquinazoline, 5.95 g of 3-(p-methoxyphenyl)-1-(4-piperidinyl)pyrrolidin-2,5-dione and 125 ml of isoamyl alcohol is refluxed for 24 hours. After standing at room temperature for two days it is filtered, the residue washed with isoamyl alcohol and diethyl ether, dried and dissolved in aqueous sodium carbonate. The solution is extracted with methylene chloride, the extract evaporated and 8.1 g of the residue dissolved in 175 ml of ethanol with warming. After addition of 1.5 g of methane sulfonic acid, a precipitate forms, which is recrystallized from aqueous ethanol to yield the 1-[1-(4-amino-6,7-dimethoxy-2-quinazolinyl)-4-piperidinyl]-3-(p-methoxyphenyl)-pyrrolidin-2,5-dione monomesylate melting at 189°–192°.

Analogously (or according to Example 2) the 1-[1-(4-amino-6,7-dimethoxy-2-quinazolinyl)-4-piperidinyl]-3-(3,4-dimethoxyphenyl)-pyrrolidin-2,5-dione monomesylate is obtained, melting at 180°–182°.

The starting material is prepared as follows: The mixture of 57.9 g of 2-(p-methoxyphenyl)-succinic anhydride, 26.3 g of 4-aminopyridine and 500 ml of xylene is refluxed on a water separator while stirring for 6.5 hours. The hot solution is decanted off, cooled, filtered and the residue recrystallized from ethanol, to yield the 3-(p-methoxyphenyl)-1-(4-pyridyl)-pyrrolidin-2,5-dione melting at 179°–180°; its 3,4-dimethoxy-analog melts at 172°–174°.

The mixture of 36 g thereof, 22 g of 10% palladium on carbon and 400 ml of glacial acetic acid is hydrogenated at 100° and 1.7 atm. After the theoretical amount of hydrogen has been taken up, the mixture is cooled, filtered and evaporated. The residue is dissolved in 100 ml of water, the solution basified with sodium carbonate, extracted with methylene chloride and the extract evaporated, to yield the 3-(p-methoxyphenyl)-1-(4-piperidinyl)-pyrrolidin-2,5-dione; the hydrochloride thereof melts at 244°–246° and its 3,4-dimethoxy-analog melts at 238°–240° respectively.

Example 12

The mixture of 6 g of 3-methyl-3-phenyl-1-(4-piperidinyl)-pyrrolidin-2,5-dione, 4.79 g of 4-amino-2-chloro-6,7-dimethoxy-quinazoline and 200 ml of isomyl alcohol is refluxed for 9 hours, cooled and acidified with anhydrous hydrogen chloride in ethyl acetate. It is filtered, the residue washed with isoamyl alcohol and diethyl ether, triturated with 95% aqueous ethanol and taken up in aqueous sodium carbonate. The solution is extracted with ethyl acetate, the extract evaporated and the residue dissolved in 100 ml of ethanol. The solution is combined with 1.6 g of methane sulfonic acid, the precipitate formed filtered off and recrystallized from aqueous ethanol, to yield the 1-[1-(4-amino-6,7-dimethoxy-2-quinazolinyl)-4-piperidinyl]-3-methyl-3-phenyl-pyrrolidin-2,5-dione monomesylate melting at 286°–290°.

The starting material is prepared as follows: The mixture of 68.6 g of 2-methyl-2-phenylsuccinic anhydride, 34 g of 4-aminopyridine and 675 ml of xylene is refluxed on a water separator while stirring for 7 hours. It is cooled to 40°, filtered, cooled to 0° and filtered again. The second residue is recrystallized from isopropanol-hexane, to yield the 3-methyl-3-phenyl-1-(4-pyridyl)-pyrrolidin-2,5-dione melting at 90°–92°.

The mixture of 36 g thereof, 22 g of 10% palladium on carbon and 400 ml of glacial acetic acid is hydrogenated at 100° and 1.7 atm. It is cooled, filtered, the residue taken up in aqueous sodium carbonate and ethyl acetate, the organic solution washed with water, dried and evaporated, to yield the 3-methyl-3-phenyl-1-(4-piperidinyl)-pyrrolidin-2,5-dione; its hydrochloride melts at 212°–214° after recrystallization from ethanol.

Example 13

The mixture of 6.16 g of 3-methyl-1-(4-piperidinyl)-pyrrolidin-2,5-dione, 6.71 g of 4-amino-2-chloro-6,7-dimethoxyquinazoline and 125 ml of isoamyl alcohol is refluxed with stirring for 18 hours. It is cooled, filtered, the solids washed with isoamyl alcohol and diethyl either, triturated with hot 90% aqueous ethanol and on cooling the crystalline product is filtered off. It is dissolved in 10% aqueous sodium carbonate, the solution extracted with ethyl acetate, the extract washed with aqueous sodium carbonate and water, dried and evaporated. The residue is dissolved in 100 ml of anhydrous ethanol with warming, 2.14 g of methane sulfonic acid are added and after cooling, the product is filtered off and recrystallized from 66% aqueous ethanol, to yield the 1-[1-(4amino-6,7-dimethoxy-2-quinazolinyl)-4-piperidinyl]-3-methylpyrrolidin-2,5-dione monomesylate melting at 325°–326° with decomposition.

The starting material is prepared as follows: The mixture of 28.5 g of 2-methylsuccinic anhydride, 23.5 g of 4-aminopyridine and 350 ml of xylene is refluxed on a water separator while stirring for 3.5 hours. The hot solution is decanted from some gummy residue, cooled, filtered, the residue suspended in 100 ml of boiling isopropanol and filtered off again, to yield the 3-methyl-1-(4-pyridyl)-pyrrolidin-2,5-dione melting at 119°–120°.

The mixture of 34.6 g thereof, 9 g of 10% palladium on carbon and 400 ml of glacial acetic acid is hydrogenated at 110° C. and approximately 1.7 atm. until the theoretical amount of hydrogen has been absorbed. The mixture is filtered, evaporated and the residue taken up in water. The pH of the mixture is adjusted to 9–10 with sodium carbonate and the liberated base extracted with methylene chloride. The extract is dried and evaporated, to yield the 3-methyl-1-(4-piperidinyl)-pyrrolidin-2,5-dione, which is used directly without further purification.

Example 14

The mixture of 4.6 g of 4-phenyl-1-(4-piperidinyl)-piperidin-2,6-dione, 3.64 g of 4-amino-2-chloro-6,7-dimethoxyquinazoline and 100 ml of isoamyl alcohol is refluxed with stirring for 22 hours. After cooling and acidifying with anhydrous hydrogen chloride in ethyl acetate, the solids are filtered off and washed with isoamyl alcohol and diethyl ether. After trituration with 90% aqueous ethanol, they are taken up in aqueous sodium carbonate, the mixture extracted with chloroform and the extract evaporated. The residue is dissolved in 75 ml of ethanol and 0.58 g of methane sulfonic acid are added. The resulting suspension is filtered and the residue recrystallized from aqueous ethanol to yield the 1-[1-(4-amino-6,7-dimethoxy-2-quinazolinyl)-4-piperidinyl]-4-phenylpiperidin-2,6-dione monomesylate melting at 292°–295° with decomposition.

Analogously the 1-[1-(4-amino-6,7-dimethoxy-2-quinazolinyl)-4-piperidinyl]-4-(p-methoxyphenyl)-piperidin-2,6-dione monomesylate is obtained, melting at 305°–307° (dec.).

The starting material is prepared as follows: The mixture of 19 g of 3-phenylglutaric anhydride, 10.3 g of 4-aminopyridine, 350 ml of xylene and 2.5 g of methane sulfonic acid is refluxed on a water separator while stirring for 2 days. The hot solution is decanted from some insolubles, cooled, filtered an the residue triturated with hot isopropanol, to yield the 4-phenyl-1-(4-pyridyl)-piperidin-2,6-dione melting at 229°–230°; the analogously prepared 4-(p-methoxyphenyl)-1-(4-pyridyl)-piperidine-2,6-dione melts at 168°–169°.

The mixture of 14.6 g of 4-phenyl-1-(4-pyridyl)-piperidin-2,6-dione, 12.3 g of 10% palladium on carbon and 200 ml of glacial acetic acid is hydrogenated at 1.7 atm. and 100° for 8 hours. After cooling, the mixture is filtered, evaporated, the residue dissolved in the minimum amount of water and the solution basified with sodium carbonate. It is extracted with ethyl acetate, the extract evaporated and the residue crystallized by trituration with 75 ml of diethyl ether-hexane (3:1) and recrystallized from 50 ml of isopropanol to yield the 4-phenyl-1-(4-piperidinyl)-piperidin-2,6-dione nelting at 182°–189°; its p-methoxyphenyl analog melts at 127°–129°.

Example 15

The mixture of 4.79 g of 4-amino-2-chloro-6,7-dimethoxyquinazoline, 5.2 g of 2-(4-piperidinyl)-hexahydroisoindole-1,3-dione and 100 ml of isoamyl alcohol is stirred under nitrogen at reflux for 20 hours. It is cooled and made acidic by addition of a solution of anhydrous hydrogen chloride in ethyl acetate. The solids obtained are filtered off, washed with ethanol, triturated with aqueous sodium carbonate, and the solution extracted with ethyl acetate. The extract is washed with water, dried, evaporated and the residue dissolved in anhydrous ethanol. The solution is neutralized with methane sulfonic acid, the precipitate formed filtered off and recrystallized from aqueous ethanol, to yield the 2-[1-(4-amino-6,7-dimethoxy-2-quinazolinyl)-4-piperidinyl]-hexahydroisoindole-1,3-dione monomesylate melting at 303°–305°.

The starting material is prepared as follows: The mixture of 23.5 g of 4- aminopyridine, 38.5 g of cis-1,2-cyclohexanedicarboxylic acid anhydride and 400 ml of xylene is refluxed for 42 hours while stirring and separating the water formed. After the first half-hour, and after 18 hours, 1 ml of methane sulfonic acid is added to the mixture. It is filtered hot, the crystals formed after cooling are filtered off and recrystallized from isopropanol, to yield the 2-(4-pyridyl)-hexahydroisoindole-1,3-dione melting at 165°–168°.

The mixture of 38.7 g thereof, 10 g of 5% rhodium on alumina and 400 ml of glacial acetic acid is hydrogenated at 3 atm. and 75°–105° for 3 hours. After cooling, the solution is filtered, evaporated, the residue treated with saturated aqueous sodium carbonate and extracted with methylene chloride. The extract is washed with water, dried and evaporated, to yield the 2-(4-piperidinyl)-hexahydroisoindole-1,3-dione; the hydrochloride thereof melts at 241°–243°.

Example 16

The mixture of 2.2 g of 4-amino-2-chloro-6,7-methylenedioxy-quinazoline, 2.2 g of 1-(4-piperidinyl)-pyrrolidin-2,5-dione and 60 ml of isoamyl alcohol is refluxed with stirring for 20 hours. It is cooled, filtered, the solids washed with isoamyl alcohol and diethyl ether and dried. The residue is triturated with 10% aqueous sodium carbonate, the solution extracted with ethyl acetate, the extract washed with aqueous sodium carbonate and water, dried and evaporated. The residue is dissolved in anhydrous ethanol with warming, and the solution neutralized with methane sulfonic acid. The precipitate formed after cooling is filtered off and recrystallized from aqueous ethanol, to yield the 1-[1-(4-amino-6,7-methylenedioxy-2-quinazolinyl)-4-piperidinyl]-pyrrolidin-2,5-dione monomesylate melting at 348° to 350° with decomposition.

In the analogous manner, preferably according to Examples 1, 12 and 13, the 1-[1-(4-amino-6,7-dimethoxy-2-quinazolinyl)-4-piperidinyl]-3,3-dimethylpyrrolidin-2,5-dione monomesylate and the 1-[1-(4-amino-6,7-dimethoxy-2-quinazolinyl)-4-piperidinyl]-3,4-dimethylpyrrolidin-2,5-dione mononesylate are prepared, melting at 267°–268° and 314°–315° respectively.

Example 17

The mixture of 3.75 g of 8-(3-piperidinyl)-8-azaspiro[4,5]decan-7,9 -dione, 3.59 g of 4-amino-2-chloro-6,7-dimethoxyquinazoline and 100 ml of isoamyl alcohol is stirred and refluxed under nitrogen for 24 hours. It is cooled to 20°, the solids filtered off, washed with isoamyl alcohol and diethyl ether and recrystallized from the mixture of 160 ml of methanol and 110 ml of water, to yield the 8-[1-(4-amino-6,7-dimethoxy-2-quinazolinyl)-3-piperidinyl]-8-azaspiro[4,5]decan-7,9-dione hydrochloride melting at 311°–312° with decomposition.

5.4 g thereof are suspended in 100 ml of water and the suspension basified with 10% aqueous sodium carbonate. It is extracted with methylene chloride, the extract dried, evaporated and the residue dissolved in 50 ml of ethanol with warming. The solution is combined with 1.1 g of methane sulfonic acid, and the precipitate formed collected, to yield the 8-[1-(4-amino-6,7-dimethoxy-2-quinazolinyl)-3-piperidinyl]-8-azaspiro[4,5]decan-7,9-dione monomesylate monohydrate melting at 195°–199°.

The starting material is prepared as follows. The mixture of 16.8 g of 3,3-tetramethyleneglutaric anhydride, 9.4 g of 3-aminopyridine and 225 ml of xylene is stirred and refluxed for 48 hours while collecting the water formed. After cooling in the refrigerator the precipitate obtained is filtered off and recrystallized from 300 ml ethanol-hexane, to yield the 8-(3-pyridyl)-8-azaspiro[4,5]decan-7,9-dione melting at 153°–154°.

The solution of 14.7 g thereof in 150 ml of glacial acetic acid is hydrogenated over 11 g of 10% palladium on carbon and 3.1 atm. at 60° until the calculated amount of hydrogen has been absorbed. The mixture is cooled to 20°, filtered and evaporated. The residue is taken up in 6N aqueous sodium hydroxide and the mixture extracted with methylene chloride. The extract is washed with saturated aqueous sodium chloride, dried and evaporated. The residual oil is dissolved in 50 ml of isopropanol and the solution acidified with hydrogen chloride. After cooling in an ice bath the precipitate formed is filtered off, dried, and this hydrochloride (m.p. 245°–248°) reconverted into the free base with 10% aqueous sodium carbonate and extracting it with methylene chloride, to yield the 8-(3-piperidinyl)-8-azaspiro[4,5]decan-7,9-dione as a viscous oil.

Example 18

The mixture of 215 g of 4-amino-2-chloro-6,7-dimethoxyquinazoline, 192.3 g of 1-(4-piperidinyl)-pyrrolidine-2,5-dione and 5,600 ml of isoamyl alcohol is stirred and refluxed for 22 hours. It is cooled to 20°, filtered and the residue washed once with 250 ml of cold ethanol and twice with 250 ml of diethyl ether each. The solids are suspended in 6000 ml of ethanol and 300 ml of water, the suspension heated to reflux, immediately cooled to 20° and filtered. The residue is washed with 300 ml of cold ethanol and 200 ml of diethyl ether, to yield the 1-[1-(4-amino-6,7-dimethoxy-2-quinazolinyl)-4-piperidinyl]-pyrrolidin-2,5-dione hydrochloride melting at 237° with decomposition.

108 g thereof are suspended in 1,500 ml of water, the suspension stirred for 30 minutes at room temperature, and combined with 2000 ml of methylene chloride, followed by the solution of 70 g of sodium carbonate in 700 ml of water. The mixture is stirred vigorously for 40 minutes at room temperature, filtered through diatomaceous earth and the residue washed with 200 ml of methylene chloride. The filtered organic layer is separated, washed with 500 ml of water, dried, treated with 10 g of charcoal, filtered again through diatomaceous earth and the filterate evaporated, to yield the corresponding free base melting at 243°–244°.

400 g thereof are suspended in 7,400 ml of 95% aqueous ethanol and 3,720 ml of water, and the suspension is combined with the solution of 102 g of methane sulfonic acid in 350 ml of 95% ethanol and 150 ml of water. The mixture is heated to 60°–65° while stirring until all solids are dissolved. The solution is allowed to cool slowly to 5° while stirring for 20 hours. It is filtered, the residue washed with 400 ml of cold 95% ethanol, 200 ml of water and 300 ml of 95% ethanol again and dried at 75° under reduced pressure for 6 hours, to yield the 1-[1-(4-amino-6, 7-dimethoxy-2-quinazolinyl)-4-piperidinyl]-pyrrolidin-2,5-dione monomesylate melting at 327°–328° with decomposition, it is identical with that obtained according to Example 1.

The starting material is prepared as follows: The mixture of 500 g of succinic acid anyhydride, 471 g of 4-amino-pyridine and 5,200 ml of xylene is heated to reflux while stirring and separating the water formed. After 30 minutes 15 ml of methane sulfonic acid are added and refluxing is continued until 5 moles of water are collected, requiring about 4 days. The mixture is cooled to room temperature, the supernatant is decanted off and the suspension combined with 1000 ml of isopropanol. It is stirred for 5 minutes, filtered, the residue washed with 250 ml of isopropanol and dried for 3 days under reduced pressure at room temperature and shortly at 50°, to yield the 1-(4-pyridyl)-pyrrolidin-2, 5-dione melting at 232°–235°.

The mixture of 213 g thereof, 40 g of 5% palladium on carbon and 750 ml of glacial acetic acid is hydrogenated at 110° and 3.4 atm. until the theoretical amount of hydrogen has been absorbed (7 hours). The mixture is filtered, evaporated, the residue taken up in 300 mol of toluene and the solution again evaporated. The residue is dissolved in 650 ml of anhydrous ethanol and the solution combined with 400 ml of saturated hydrogen chloride in ethyl acetate. The precipitate formed on cooling to 5° is filtered off and washed with 100 ml of ethanol-diethyl ether (1:1 ) and 200 ml of diethyl ether, to yield the 1-(4-piperidinyl)-pyrrolidin-2,5-dione hydrochloride melting, after recrystallization from ethanol, at 283°–284°.

The solution of 847.7 g thereof in 8,200 ml of methanol is combined with 209 g of sodium methylate in 2,200 ml of methanol and the mixture is cooled to 5°. After addition of 25 g of charcoal it is filtered through diatomaceous earth and the residue washed with 300 ml of methanol. The combined filtrates are concentrated to 1,800 ml, filtered, evaporated and the residue cooled at 60° in vacuo, to yield the corresponding free base melting at 122 °–135° ; after purification it is identical with that obtained according to Example 1.

EXAMPLE 19

Preparatin of 10,000 tablets each containing 2.5 mg of the active ingredient:

Formula

| | |
|---|---|
| 1-[1-(4-amino-6,7-dimethoxy-2-quinzolinyl)-4-piperidinyl]-pyrrolidin-2,5-dione monomesylate | 25.00 g |
| Lactose | 1,956.00 g |
| Corn starch | 90.00 g |
| Polyethylene glycol 6,000 | 90.00 g |
| Talcum powder | 90.00 g |
| Magnesium stearate | 24.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 45 ml of the water and the suspension added to the boiling solution of the polyethylene glycol in 180 ml of water. The paste formed is added to the powders which are granulated, if necessary, with an additional amount of water. The granulate is dried overnight at 35°, broken on a screen with 1.2 mm openings and compressed into tablets using concave punches with 7.1 diameter, uppers bisected.

Preparation of 10,000 capsules each containing 5 mg of said active ingredient:

Formula

| | |
|---|---|
| Said monomesylate | 50.0 g |
| Lactose | 2,350.0 g |
| Talcum powder | 150.0 g |

Procedure

All the powders are passed through a screen with openings of 0.6 mm. Then the drug substance is placed into a suitable mixer and mixed first with the talcum, then with the lactose until homogenous. No. 2 capsules are filled with 300 mg, using a capsule filling machine.

Analogously tablets and capsules are prepared from the remaining compounds of the invention, e.g. those illustrated by the other examples herein.

What is claimed is:

1. An N-[1-(4-amino-2-quinazolinyl)-3 or 4-piperdinyllactam of the formula

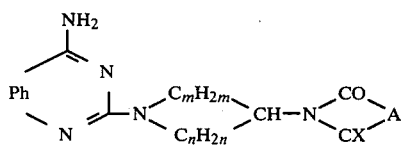

wherein Ph is 1,2-phenylene, unsubstituted or substituted by up to 3 lower alkyl or lower alkoxy groups, or by one lower alkylenedioxy group; each of m and n is an integer from 1 to 3, but m+n=4; X represents 2 hydrogen atoms or oxo and A is lower alkylene, 4 to 7 ring-membered cycloalkylene, cycloalkyl-lower alkylene, spirocycloalkane-lower alkylene, H-Ph-lower alkylene or Ph; or a pharmaceutically acceptable acid addition salt thereof.

2. A compound as claimed in claim 1, wherein Ph is 1,2-phenylene, unsubstituted or substituted by up to 3 alkyl or alkoxy groups with up to 4 carbon atoms or one alkylenedioxy group with up to 2 carbon atoms; each of m and n is an integer from 1 to 3, but m+n=4; X represents 2 hydrogen atoms or oxo and A is lower alkylene, 4 to 7 ring-membered cycloalkylene, cycloalkyl-lower alkylene, sprirocycloalkane-lower alkylene, HPh-lower alkylene or Ph; or a pharmaceutically acceptable acid addition salt thereof.

3. A compound as claimed in claim 1, wherein Ph is 1,2-phenylene, mono-, di-or tri-(alkyl or alkoxy)-1,2-phenylene or alkylenedioxy-1,2-phenylene wherein alkyl or alkylene contains up to 2 carbon atoms; each of $C_mH_{2m}$ and $C_nH_{2n}$ is ethylene; X represents 2 hydrogen atoms or oxo and A is lower alkylene, or 5 or 6 ring-membered 1,2-cycloalkylene or (cycloalkyl, spirocycloalkane or phenyl)-alkylene with up to 8 carbon atoms each; or a pharmaceutically acceptable acid addition salt thereof.

4. A compound as claimed in claim 1 wherein the Ph-substituents occupy the 6,7- or 6,7, 8-quinazolinyl positions.

5. A compound as claimed in claim 4 and having the formula

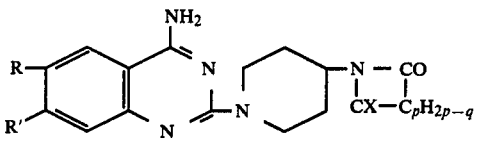

wherein R and R' are methoxy or together methylenedioxy; X represents two hydrogen atoms or oxo; $C_pH_{2p-q}$ is alkylene, phenylalkylene or spirocycloalkane-alkylene wherein p is an integer from 2 to 8, q is the integer 0, 2 or 8, and 2 p−q is positive; or a pharmacetically acceptable acid addition salt thereof.

6. A compound as claimed in claim 5, wherein each of R and R' are methoxy; X is oxo and $C_pH_{2p-q}$ is ethylene, phenylethylene or 1,3-propylene; or a pharmaceutically acceptable acid addition salt thereof.

7. A compound as claimed in claim 5 and being the 1-[1-(4-amino-6,7-dimethoxy-2-quinazolinyl)-4-piperidinykl]-pyrrolidin-2,5-dione, or a pharmaceutically acceptable acid addition salt thereof.

8. A compound as claimed in claim 5, and being the 1-[1-(4-amino-6,7-dimethoxy-2-quinazolinyl)-4-piperidinyl]-3-phenylpyrrolidin-2,5-dione, or a pharmaceutically acceptable acid addition salt thereof.

9. An antihypertensive pharmaceutical composition comprising a hypotensively effective amount of a compound as claimed in claim 1, together with a pharmaceutical excipient.

10. The method of treating hypertension and congestive or chronic heart failure in mammals, which comprises administering to said mammals enterally or parenterally an effective dosage of a composition as claimed in claim 9.

* * * * *